United States Patent [19]
Komatsu et al.

[11] 4,290,969
[45] Sep. 22, 1981

[54] PROCESS FOR THE CONTINUOUS PRODUCTION OF POLYISOCYANATE

[75] Inventors: Kazurou Komatsu; Sojiro Matsumoto; Takeshi Maniwa; Nobuyuki Shinmura, all of Hyuga, Japan

[73] Assignee: Asahi Kasei Kogyo Kabushiki Kaisha, Osaka, Japan

[21] Appl. No.: 177,961

[22] Filed: Aug. 14, 1980

[51] Int. Cl.³ .............. C07C 119/042; C07C 127/24
[52] U.S. Cl. .................... 260/453 AB; 260/453 A; 260/453 AL; 260/453 AR
[58] Field of Search ..... 260/453 A, 453 AB, 453 AL, 260/453 AR

[56] References Cited

U.S. PATENT DOCUMENTS

| 3,124,605 | 3/1964 | Wagner | 260/453 AB |
|---|---|---|---|
| 3,350,438 | 10/1967 | Hennig | 260/453 AB |
| 3,358,010 | 12/1967 | Britain | 260/453 AB |
| 3,392,183 | 7/1968 | Windemuth et al. | 260/453 AB |
| 3,903,127 | 9/1975 | Wagner et al. | 260/453 AB |
| 4,176,132 | 11/1979 | Ide et al. | 260/453 A |

Primary Examiner—Dolph H. Torrence
Attorney, Agent, or Firm—Sughrue, Mion, Zinn, Macpeak and Seas

[57] ABSTRACT

A process for the continuous production of a polyisocyanate by reacting an organic diisocyanate with an adduct-producing agent that reacts with an isocyanato group to form an intermediate product having a urea bond and a gas is disclosed wherein the initial stage of the reaction is performed in one or two continuous complete mixing type reactors until the amount of gas generated is at least about 80% of the amount of gas to be generated during the entire reaction and the subsequent stage of the reaction is performed in a plug flow reactor.

13 Claims, 1 Drawing Figure

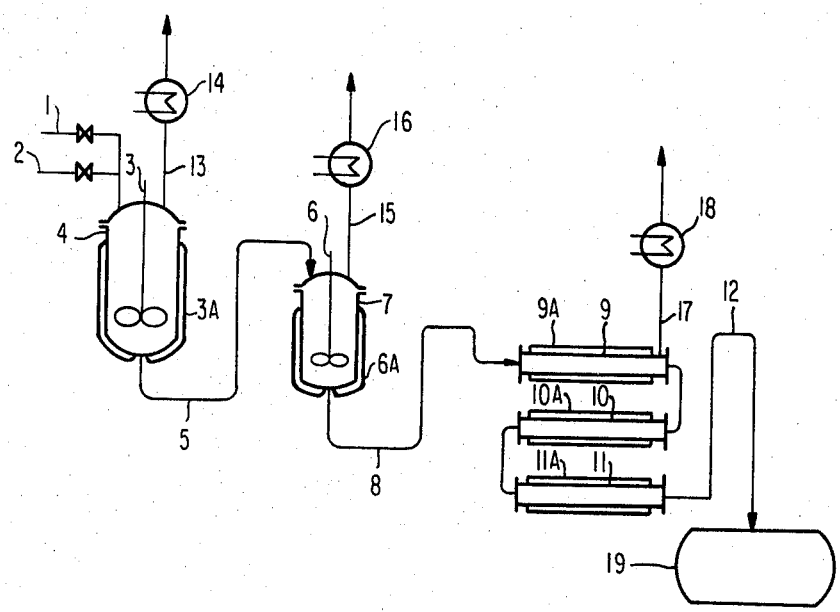

PROCESS FOR THE CONTINUOUS PRODUCTION OF POLYISOCYANATE

BACKGROUND OF THE INVENTION

1. Field of the Invention

This invention relates to a continuous process for the production of a polyisocyanate.

2. Description of the Prior Art

The method of producing a polyisocyanate by reacting an organic diisocyanate with an adduct-producing agent which reacts with an isocyanate group to form a urea bond and a gas is known. Examples of the organic diisocyanate are alicyclic diisocyanates and aliphatic diisocyanates, such as hexamethylene diisocyanate. Examples of the adduct-producing agent are water, monovalent tertiary alcohol, formic acid, hydrogen sulfide and organic primary monoamine. Generally, the organic diisocyanate is used in excess with respect to the adduct-producing agent, for example, at least about 3 mols, preferably at least about 10 mols of the organic diisocyanate is used per mol of the adduct-producing agent.

The reaction of the organic diisocyanate with the adduct-producing agent is characterized by the formation of a urea bond and generation of a gas, as is shown in the following reaction schemes:

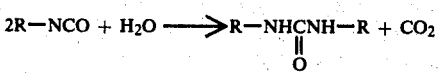

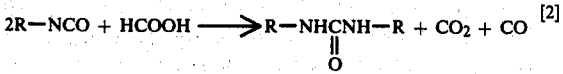

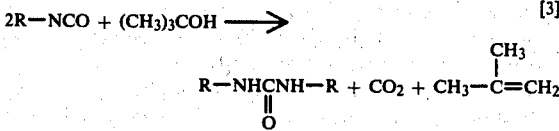

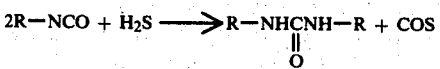

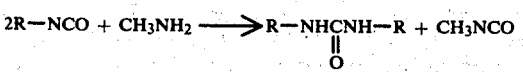

The urea bond thus-formed further reacts with an isocyanato group to form a 3 or more functional organic polyisocyanate. For example, a urea dimer reacts with a diisocyanate monomer to form a trifunctional polyisocyanate trimer. The resulting polyisocyanate is typically either a viscous liquid or a solid. However, such a solid polyisocyanate is highly soluble in common organic solvents such as toluene, xylene and acetic acid esters.

As shown above, the reaction between the organic diisocyanate and adduct-producing agent is consecutive, but the urea dimer or urea bond-containing oligomers formed in the course of the reaction are solids, and are so low in miscibility with the reaction mixture and the polyisocyanate product that they can form a precipitate that blocks the production equipment or produces a turbid liquid polyisocyanate. Thus, it is undesirable that a urea bond remains not further reacted with an isocyanate group. Even a polyisocyanate free from urea bonds is highly viscous if its molecular weight is great, and such viscous polymer is so low in miscibility with other resins or solvent that it cannot be used in combination with a polyhydroxy compound as a paint without adversely effecting the film-forming properties and physical properties of the paint. To produce low molecular weight polyisocyanate free from urea bonds, the conventional method uses the organic diisocyanate in excess with respect to the adduct-producing agent, as described above, but the use of a great excess of the organic diisocyanate, (e.g., more than 40 mols per mol of the adduct-producing agent) has its own problems, viz., not only must the excess diisocyanate be recovered, but also the organic diisocyanate used enters into thermal polymerization to produce a strongly colored polyisocyanates including, for instance, uretidion rings, isocyanurate rings, and/or carbodimide bonds. To prevent these disadvantages, the organic diisocyanate is used generally in an amount of from 5 to 40 mols, and preferably from 10 to 30 mols, per mol of the adduct-producing agent.

The reaction between the organic diisocyanate and adduct-producing agent is conventionally performed in a batchwise reactor. The batchwise reaction is characterized by a uniform residence time of the reactants in the reactor which is desirable for providing a polymer having a narrow range of molecular weight. However, a batchwise reaction performed on an industrial scale is inefficient, because it involves a complex and troublesome operation that may lead to improper sequence of operations and/or an accident. Furthermore the quality of the polyisocyanate produced by the batchwise reaction differs from batch to batch.

However, attempts to perform the reaction between the organic diisocyanate and adduct-producing agent in a continuous manner involve the following problems: (a) Even if all stages of the reaction are performed in a single continuous stirring tank reactor to provide a homogeneous mixture, it is practically impossible to keep the residence time of the mixture of reactants uniform. In other words, part of the liquid mixture of reactants may reside in the reactor for only a short period of time and another part resides for a longer period, thus producing a by-product that has an unreacted urea group or a product having a very large molecular weight. It is thus difficult to keep producing a polyisocyanate of high quality by the continuous process. (b) If all stages of the reaction are performed in a pipe reactor that provides a perfect plug flow or through a series of connected continuous stirring tank reactors to provide a substantially plug flow, the residence time in theory can be maintained uniformly, and the above problems seem avoidable. However, in fact, even a pipe reactor cannot provide a perfect plug flow in a reaction of the type contemplated by this invention that involves the generation of a gas, because the gas generated causes turbulence or convection in the liquid reaction mixture. A plurality of partitions such as baffles may be used to divide the pipe reactor into compartments, but local residence of the reaction mixture or uneven distribution of temperature in the initial period of the reaction unavoidably results in the formation of an unreacted urea compound or a polymer. Connecting continuous stirring tank reactors is effective for preventing the turbulence of the liquid reaction mixture due to gas generation, but the use of a plurality of continuous stirring tank reactors for providing a substantial plug flow is not an economical method to adopt on an industrial scale.

SUMMARY OF THE INVENTION

Therefore, the primary object of this invention is to provide an industrially efficient process that continuously produces low-viscosity, transparent polyisocyanate while inhibiting the formation of a urea group-containing compounds and polymer of high molecular weight.

As a result of extensive studies to overcome the defects of the conventional techniques, an efficient continuous process has now been found for producing a transparent, low-viscosity polyisocyanate having a narrow distribution of molecular weight by performing the initial stage of the reaction between an organic diisocyanate and an adduct-producing agent capable of reacting with an isocyanate group to form an intermediate product having a urea bond and a gas in one or two continuous complete mixing type reactors until the amount of gas generated is at least about 80% of the amount of gas to be generated during the entire reaction and by performing the subsequent stage of the reaction in a plug flow reactor. It is indeed unexpected that this invention produces a low-viscosity polyisocyanate having a molecular weight distribution equal to that produced in the conventional batchwise reaction in spite of the fact that most of the reaction is performed continuously in one or two continuous complete mixing type reactors.

BRIEF DESCRIPTION OF THE DRAWING

The FIGURE is a flow sheet showing one embodiment of the apparatus used in continuous production of a polyisocyanate according to this invention.

DETAILED DESCRIPTION OF THE INVENTION

Continuous complete mixing type reactors to be used in the process of this invention may be such a reactor providing a substantially homogeneous mixture, for example, a continuous stirring tank reactor mounted a motor-drive stirrer. Plug flow type reactors to be used in the process of this invention may be such a reactor providing substantially uniform residence time flow; which includes a pipe reactor, a perforated plate column reactor and a multiple-stage stirring tank reactor with baffle plates.

In the practice of this invention, one or two continuous stirring tank reactors are used to perform the first stage of the reaction under stirring to provide a homogeneous mixture. Preferably, two such tanks are used connected in series. A plurality of series-connected continuous stirring tank reactors or a pipe reactor may be used to perform the subsequent stage of reaction under conditions to provide substantially a plug flow of the reaction mixture. Partitions may be used to divide the pipe reactor into compartments so as to aid in providing a plug flow. For economy in initial cost, a pipe reactor is preferably used for the subsequent stage of reaction in this invention wherein the first stage of the reaction has been performed in a continuous stirring tank reactors.

An exact definition of the initial stage of the reaction can not be determined by such factors as residence time, because it varies with operating conditions of the process, but it is generally such that the amount of gas generated by the reaction between the organic isocyanate and adduct-producing agent reaches at least about 80%, and preferably at least about 90%, of the amount of gas generated during the entire reaction. If the value is less than about 80%, much gas is generated in the latter stage of the reaction to prevent the formation of a substantial plug flow and the quality of the resulting polyisocyanate is not what is desired in this invention. Since the concentration of a urea dimer is high in the initial period of the reaction, it may locally form a deposit on the wall of the reactor or piping, and this deposit will grow into polyurea of high molecular weight, and block the piping and/or have an adverse effect on the resulting polyisocyanate. It is therefore necessary that most of the reaction be performed under stirring, but it should be understood that an excessively long residence time can cause excessive polymerization that gives a polymer of large molecular weight and produces a highly viscous, colored polyisocyanate. The initial stage of the reaction is preferably performed at a temperature in the range of from about 80° to about 180° C. At temperature lower than 80° C., the formation of product that contains a urea bond is unavoidable no matter how long the residence time may be. Temperatures higher than 180° C. may result in a polymer of large molecular weight. The residence time, which is determined by the amount of the gas generated is generally in the range of from about 30 to 240 minutes.

If the initial stage of the reaction is performed in two continuous stirring tank reactors connected in series, the reaction in the first reactor is carried out until the amount of gas generated is at least about 60% of the amount of gas generated during the entire reaction, and the reaction in the second reactor is carried out until the sum of the gases generated in the first and second reactors is at least about 80% of the amount of gas generated during the entire reaction. In the second reactor, the urea bond in the intermediate compound formed in the first reactor is further reacted with the organic diisocyanate to form a polyisocyanate. The reaction is performed at a temperature generally 0° to 80° C. higher than the temperature of the reaction in the first reactor. The primary purpose of the reaction in the second reactor is to prevent the presence of a residual polyurea compound. The reaction in the second reactor can be omitted if the reaction in the first reactor has already proceeded to such a degree that the amount of gas generated is at least about 80% of the amount of gas to be generated during the entire reaction. A suitable residence time for the reaction in the second reactor is in the range of from 5 to 240 minutes.

The subsequent stage of the reaction of this invention is performed so that the intermediate urea bond that has not been used in the initial period is further reacted with the diisocyanate. As already mentioned, this stage of the reaction is performed in a pipe reactor or continuous stirring tank reactors under conditions to provide a substantial plug flow in such a manner that the compound containing a urea bond will not be carried into the final product. Therefore, a gas, which causes turbulence or convection in the plug flow, should desirably not be generated in large amounts in this stage. The reaction mixture entering into the subsequent stage of the reaction must be such that the amount of gas generated exceeds about 80% of the amount of gas generated during the entire reaction. The reaction temperature is preferably from about 0° to 80° C. higher than that at the end of the initial stage of the reaction, for example, the reaction temperature in the first reactor. An average residence time should be in the range of from about 30 to 240 minutes. As mentioned before, a pipe reactor is preferably used to perform the reaction under conditions to provide a plug flow. The pipe length depends on the desired residence time, but generally it is at least about 15 times, and preferably at least about 30 times, larger than the pipe diameter. Since some gas is generated in the latter stage of the reaction, the pipe may be divided into sections by one or more partitions, such as baffles, to facilitate the formation of plug flow. The pipe may also be provided with vent holes.

Any organic diisocyanate can be used in this invention, and aliphatic and/or araliphatic diisocyanates are preferred such as tetramethylene diisocyanate, hexamethylene diisocyanate, cyclohexylene-1,2-diisocyanate, hexahydroxylene diisocyanate, an isomer mixture of 1-methyl-2,4-diisocyanato-cyclohexane and 1-methyl-2,6-diisocyanato-cyclohexane, bis-(4-isocyanatocyclohexyl)methane, 1-isocyanato-3,3,5-trimethyl-5-isocyanatomethyl-cyclohexane (isophorone diisocyanate), 2,6-diisocyanate-capronic acid ester, and m- and p-xylylene diisocyanate. Of these, tetramethylene diisocyanate, hexamethylene diisocyanate, isophorone diisocyanate and m- and p-xylene diisocyanate are particularly preferred. If the polyisocyanate to be produced need not have yellowing resistance, an aromatic diisocyanate can also be used, such as 1-methylbenzene-2,4-diisocyanate, 1-methylbenzene-2,6-diisocyanate, an isomer mixture of the previous two, and methylene-bis(4-phenylisocyanate).

The adduct-producing agent used in this invention reacts with an organic diisocyanate to form a urea bond and a gas, and examples of such agent are water, formic acid, hydrogen sulfide, tertiary butanol and methylamine. These agents may be used independently or as a mixture. They may be mixed with polyhydric alcohols to produce a polyisocyanate mixture containing a urethane bond-having polyisocyanate or a copolymer thereof with polyhydric alcohols. The proportion of the organic diisocyanate to adduct-producing agent is from about 5 to 40 mols, and preferably from 10 to 30 mols, of the organic diisocyanate per mole of the adduct-producing agent.

In the reaction of this invention, a solvent inert with respect to the isocyanato group can be used. A preferred solvent has a boiling point between about 80° and 200° C., dissolves both the organic diisocyanate and adduct-producing agent, and forms a homogeneous phase under reaction conditions. Illustrative preferred solvents are esters, phosphate esters, ketones, amides and ethers. Specific examples are methyl cellosolve acetate, cellosolve acetate, methyl isobutyl ketone, trimethyl phosphate, diethylene glycol dimethyl ether. The amount of the solvent used is generally in the range of from 10 to 80% by weight based on the total weight of the reaction mixture.

One embodiment of the equipment for continuous production of a polyisocyanate according to this invention is now described by reference to FIGURE. A flow of an organic diisocyanate is supplied continuously through a pipe 2 into a first reactor 4 comprising a continuous stirring tank reactor. A flow of an adduct-producing agent is also supplied through a pipe 1 into the first reactor 4. The reactor 4 comprises a stirrer 3 and a heating jacket 3A. Gas generated in the reaction is discharged through a pipe 13 and a condenser 14. The first reactor 4 is connected to the second reactor 7 by a pipe 5. The second reactor 7 is also a continuous stirring tank reactor and comprises a stirrer 6 and a heating jacket 6A. Gas generated in the reactor 7 is discharged through a pipe 15 and a condenser 16. The second reactor 7 is connected to pipe reactors 9, 10 and 11 by a pipe 8. The pipe reactors have jackets 9A, 10A and 11A, respectively, and gas generated in each pipe reactor is discharged through a pipe 17 and a condenser 18. The resulting reaction liquor is continuously drawn through a pipe 12 into an intermediate tank 19. After completion of the reaction, the excess organic diisocyanate or a mixture thereof with a solvent is recovered from the polyisocyanate product using a conventional wiped-film evaporator apparatus or extraction with a suitable solvent, such as n-hexane.

As described in the foregoing, the process of this invention involves performing continuous reaction of an organic diisocyanate and an adduct-producing agent by carrying out the initial stage of the reaction under stirring to provide a homogeneous reaction mixture and conducting the subsequent stage of reaction under conditions to provide a substantial plug flow. By so doing, this invention successfully produces a low-viscosity transparent polyisocyanate having a narrow distribution of molecular weight, and which is free from polymer of high molecular weight. Therefore, it is a great advantage of the process of this invention that it achieves continuous production of polyisocyanate on an industrial scale that has been unobtainable in the prior art.

This invention is now described in greater detail by reference to the following examples, which are given here for illustrative purposes only and are by no means intended to limit the scope of the invention.

EXAMPLE 1

Referring to FIGURE, a stirring tank equipped with a steam-heating jacket was used as each of the first reactor 4 and second reactor 7. The third reactor comprised three pipe reactors 9, 10 and 11 of equal dimension. Each pipe reactor in the third reactor had a pipe length to diameter ratio (L/D) of 10. The three reactors were connected in series and they were constructed in such a manner that the respective average residence times were 90 minutes (first reactor), 60 minutes (second reactor) and 60 minutes (third reactor). A solution of 1,000 parts by weight of hexamethylene diisocyanate in 500 parts by weight of a solvent comprising equal amounts of methyl cellosolve acetate and trimethyl phosphate was continuously supplied into the first reactor 4 at a rate of 1,000 parts by weight per hour. The first reactor was also supplied continuously with water at a rate of 4.8 parts by weight per hour. The temperatures in the first reactor 4, second reactor 7 and third reactor 9, 10 and 11 were held at 120° C., 150° C., and 160° C., respectively. In the first reactor 4, about 85% of the gas to be generated during the entire reaction was generated. In the second reactor 7, about 10% of the gas was generated, and in the third reactor, about 5% of the gas was generated. The resulting reaction liquor was freed of excess hexamethylene diisocyanate and solvent with a wiped-film evaporator apparatus. A polyisocyanate was produced at a rate of 115 parts by weight per hour; it was a highly transparent, viscous liquid with a tint of yellow having a viscosity of 1,800 cPs (25° C.) and an isocyanato content of 24.0 wt%. Analysis by gel chromatography gave the following results:

Residual monomer: 0.2%
Dimer: 7.0%
Trimer: 54.2%
Tetramer: 2.9%
Pentamer: 17.4%

Higher oligomers: 18.3%

The reactors kept producing a polyisocyanate consistent in quality over a period of several weeks without any problem.

EXAMPLE 2

Reactors identical with what were used in Example 1 were used in this example. A solution of 1,000 parts by weight of isophorone diisocyanate in 500 parts by weight of a solvent comprising equal amounts of methyl cellosolve acetate and trimethyl phosphate was supplied continuously at a rate of 1,000 parts by weight per hour. Water was also supplied continuously at a rate of 3.6 parts by weight per hour. The temperature in the first, second and third reactors was held at 120° C., 150° C. and 150° C., respectively. The amount of gas generated in the reactors was 87%, 10% and 3%, respectively, of the amount of gas to be generated during the entire reaction. A wiped-film evaporator apparatus was used to recover excess isophorone diisocyanate and solvent from the reaction product. A highly transparent, viscous polyisocyanate with a tint of yellow having a viscosity of 3,200 cPs (50° C.) and an isocyanato content of 17.3 wt% was produced at a rate of 110 parts by weight per hour. After 24 hours of continuous operation, the reactors were disassembled and their inside was inspected; a small amount of scale was detected only on the wall of the first reactor.

EXAMPLE 3

Reactors identical to those used in Example 1 were used. A solution of 1,000 parts by weight of xylylene diisocyanate in 1,000 parts by weight of a solvent comprising a mixture of equal amounts of methyl cellosolve acetate and trimethyl phosphate was supplied continuously at a rate of 1,500 parts by weight per hour. Water was also supplied continuously at a rate of 3.6 parts by weight per hour. The temperature in the first, second, and third reactors was held at 120° C., 130° C. and 130° C., respectively. The respective average residence times were 45 minutes, 45 minutes and 60 minutes. The amount of gas generated in the reactors was 90%, 8% and 2%, respectively, of the amount of gas to be generated during the entire reaction. The resulting reaction liquor was freed of the excess xylylene diisocyanate and solvent using a wiped-film evaporator apparatus. A polyisocyanate having a viscosity of 3,000 cPs (50° C.) and an isocyanato content of 22.1 wt% was produced at a rate of 108 parts by weight per hour. The product was a pale yellow, transparent viscous liquid. After two days of continuous operation, the reactors were disassembled and their inside was inspected; a small amount of scale was detected only on the wall of the first reactor.

EXAMPLE 4

Reactors identical with what were used in Example 1 were used in this example. Hexamethylene diisocyanate was continuously supplied at a rate of 1,000 parts by weight per hour, and liquid tertiary butanol was also supplied continuously at a rate of 29.3 parts by weight per hour. The temperature in the first, second and third reactors was set at 140° C., 180° C. and 180° C., respectively. The respective average residence times were 90 minutes, 90 minutes and 135 minutes. The amounts of gas generated in the respective reactors were 84%, 10% and 6% of the gas to be generated during the entire reaction. A wiped-film evaporator apparatus was used to recover excess hexamethylene diisocyanate from the reaction liquor. A pale yellow, transparent polyisocyanate having a viscosity of 1,900 cPs (25° C.) and an isocyanate content of 23.8% was produced at a rate of 115 parts by weight per hour. After 24 hours of continuous operation, the reactors were disassembled and their inside was inspected; a small amount of scale was detected only on the wall of the first reactor.

COMPARATIVE EXAMPLE 1

The procedure of Example 1 was repeated except that the average residence time in the first reactor 4 was 20 minutes. The amount of gas operated in the first reactor was 50% of the gas to be generated during the entire reaction. After 24 hours of operation, a polyurea precipitate blocked the pipe 5 connecting the first reactor 4 with the second reactor 7 and made subsequent operation impossible.

COMPARATIVE EXAMPLE 2

In this comparative example, only one continuous stirring tank reactor was used to perform a continuous operation. As such reactor, the first reactor 4 of the equipment of Example 1 was used, and the reaction liquor was designed to overflow into the intermediate tank 19 directly from the reactor through the pipe 5. The reactor was operated under the same conditions as in Example 1 except that the temperature in the reactor was 160° C. and the supply rate of the reactants was such that the average residence time in the reactor was 210 minutes. After recovering excess hexamethylene diisocyanate and solvent, a polyisocyanate having a viscosity of 2,000 cPs, an isocyanate content of 23.7 wt% and a residual hexamethylene diisocyanate content of 0.2% was obtained. The product was a viscous liquid with excessive white turbidity.

COMPARATIVE EXAMPLE 3

The procedure of Example 1 was repeated except that third reactor comprising a pipe reactor having a pipe length to diameter ratio of 7 was used instead of the third reactor comprising three pipe reactors 9, 10 and 11 and the residence time in the third reactor was 60 minutes. A polyisocyanate with white turbidity resulted.

COMPARATIVE EXAMPLE 4

In this comparative example, only a pipe reactor was used to perform a continuous operation. As such reactor, the third reactor of Example 1 comprising three pipe reactors was used. Each pipe reactor was equipped with a vent pipe near to its entrance and exit, it was provided with a steam-heating jacket. A solution of 1,000 parts by weight of hexamethylene diisocyanate in 500 parts by weight of a solvent comprising equal amounts of methyl cellosolve acetate and trimethyl phosphate was supplied continuously into each reactor at a rate of 667 parts by weight per hour. Water was also supplied continuously at a rate of 3.2 parts by weight per hour. The average residence time in the reactor was 90 minutes. The solution was supplied at room temperature, and the temperature in each pipe reactor was controlled so that it was 150° C. in the middle of the first pipe reactor, 155° C. at its exit, and 155° C. in both the second and third pipe reactors. The reaction liquor was continuously freed of excess hexamethylene diisocyanate and solvent using a wiped-film evaporator apparatus. A highly transparent polyisocyanate having a viscosity of 1,850 cPs (25° C.) was produced at a rate of 77 parts by weight per hour. However, after about 49 hours of the reaction, the operation was stopped due to pipe blocking. Inspection after disassembly revealed the presence of a large amount of polyurea scale in the area that covered the entrance to the middle of the first pipe reactor.

REFERENCE EXAMPLE

In this example, one reactor of complete mixing type was used in a batchwise reaction. A solution of 670 parts by weight of hexamethylene diisocyanate in a solvent consisting of 165 parts by weight of trimethyl phosphate and an equal amount of methyl cellosolve acetate was supplied into a reactor with a stirrer having a reflux condenser. Under stirring in a nitrogen atmosphere, 4.8 parts by weight of water was added to the solution, the temperature of which was elevated to 160° C. over a period of 120 minutes, and the solution was held at that temperature for 60 minutes under atmospheric pressure. After the reaction, no precipitate of a polyurea compound was detected in the reaction liquor. The reaction liquor was freed of unreacted hexamethylene diisocyanate and solvent using a wiped-film evaporator apparatus at 0.2 mmHg and 180° C. A pale yellow polyisocyanate (113 parts by weight) having a viscosity of 1,800 cPs (25° C.) and an isocyanato content of 23.9 wt% was produced as bottoms. Analysis by gel chromatography showed that the product comprised the following:

Monomer: 0.4%
Dimer: 7.6%
Trimer: 56.0%
Tetramer: 6.0%
Pentamer: 17.5%
Higher oligomers: 12.5%

While the invention has been described in detail and with reference to specific embodiments thereof, it will be apparent to one skilled in the art that various changes and modifications can be made therein without departing from the spirit and scope thereof.

What is claimed is:

1. A process for the continuous production of a polyisocyanate by reacting an organic diisocyanate with an adduct-producing agent that reacts with an isocyanate group to form an intermediate product having a urea bond and a gas, the initial stage of the reaction being performed in one or two continuous complete mixing type reactors until the amount of gas generated is at least about 80% of the amount of gas to be generated during the entire reaction, and the subsequent stage of the reaction is performed in a plug flow type reactor.

2. A process according to claim 1 wherein the organic diisocyanate is an aliphatic diisocyanate, an araliphatic diisocyanate, or a combination thereof.

3. A process according to claim 2 wherein the organic diisocyanate is tetramethylene diisocyanate, hexamethylene diisocyanate, isophorone diisocyanate or m- and p-xylene diisocyanate.

4. A process according to claim 1 wherein the adduct-producing agent is at least one compound selected from the group consisting of water, tertiary butanol, formic acid, hydrogen sulfide and methylamine.

5. A process according to claim 1 wherein from about 5 to 40 mols of the organic diisocyanate is used per mole of adduct-producing agent.

6. A process according to claim 1 wherein the initial stage of the reaction is performed in one continuous stirring tank reactor.

7. A process according to claim 1 wherein the initial stage of the reaction is performed in two continuous stirring tank reactors connected in series, the reaction in the first reactor is performed until the amount of gas is at least about 60% of the amount of gas to be generated during the entire reaction, and the reaction in the second reactor is performed until the total amount of gas generated in the two reactors is at least about 80% of the amount of gas to be generated during the entire reaction.

8. A process according to claim 1 wherein the subsequent stage of the reaction is performed in a pipe reactor.

9. A process according to claim 8 wherein the length of the pipe reactor is at least 15 times larger than its diameter.

10. A process according to claim 1 wherein two continuous stirring tank reactors and a pipe reactor are connected in series, the reaction in the first reactor is performed at a temperature between about 80° and 180° C. with an average residence time of from about 30 to 240 minutes until the amount of gas generated is at least about 60% of the amount of gas to be generated during the entire reaction, the reaction in the second reactor is performed at a temperature of from about 0° to 80° C. higher than the temperature in the first reactor with an average residence time between about 5 and 240 minutes until the amount of gas generated in the first and second reactors is at least about 80% of the amount of gas to be generated during the entire reaction, and the reaction in the pipe reactor is performed at a temperature of from about 0° to 80° C. higher than the temperature in the first reactor and with an average residence time between about 30 and 240 minutes.

11. A process according to claim 1 or 6 wherein the initial stage of the reaction is performed until the amount of gas generated is at least about 90% of the amount of gas to be generated during the entire reaction.

12. A process according to claim 9 wherein the length of the pipe reactor is at least 30 times larger than its diameter.

13. A process according to claim 1 wherein from about 10 to 30 mols of the organic diisocyanate is used per mol of adduct-producing agent.

* * * * *